United States Patent [19]

Servier

[11] 4,071,629

[45] Jan. 31, 1978

[54] NOVEL PHARMACEUTICAL COMPOSITIONS AND METHOD FOR TREATING PSYCHASTHENIA

[75] Inventor: Jacques Servier, Neuilly-sur-Seine, France

[73] Assignee: Science Union et Cie, Societe Francaise de Recherche Medicale, Suresnes, France

[21] Appl. No.: 718,134

[22] Filed: Aug. 27, 1976

[51] Int. Cl.² .......................... A61K 31/505
[52] U.S. Cl. .................................. 424/251
[58] Field of Search .......................... 424/251

[56] References Cited

FOREIGN PATENT DOCUMENTS 59,21M   4/1968   France.

Primary Examiner—Stanley J. Friedman
Attorney, Agent, or Firm—Gordon W. Hueschen

[57] ABSTRACT

This invention relates to pharmaceutical compositions having psychoanaleptic activity containing a thiamine disulphide derivative as active ingredient.

The novel pharmaceutical composition has therapeutical utility, namely, in the treatment of psychic and/or behavioral disturbances due to psychasthenia.

2 Claims, No Drawings

NOVEL PHARMACEUTICAL COMPOSITIONS AND METHOD FOR TREATING PSYCHASTHENIA

DESCRIPTION OF THE PRIOR ART

The prior art may be illustrated with the French drug patent No. 5921M issued on Apr. 1, 1968.

SUMMARY OF THE INVENTION

This invention relates to novel pharmaceutical compositions having as active ingredient a thiamine disulphide derivative of an amount safe and effective for treating psychasthenia.

This invention also relates to a method for treating humans suffering from psychic disturbances and/or behavioural disturbances resulting from depressive conditions.

The treatment is performed parenterally, orally, sublingually, or rectally at a daily dosage ranging from 3.3 mg/kg to 25 mg/kg of bis [(2-isobutyryloxyethyl) 1-methyl vinylene] bis N-[4-amino 2-methyl 5-pyrimidinyl methyl] formamide disulphide as active ingredient.

PREFERRED EMBODIMENTS

The present invention relates to novel pharmaceutical compositions endowed with psychotropic activity. More particularly it relates to pharmaceutical compositions possessing psychoanaleptic properties and having as active ingredient a thiamine disulfide.

Specifically the invention provides pharmaceutical compositions containing from 150 to 500 mg of bis [(isobutyryloxyethyl) methylvinylene] bis N[(4-amino 2-methyl 5-pyrimidinyl) methyl] formamide disulphide or Vitaberin in addition to or in admixture with an inert non-toxic pharmaceutical carrier.

Vitaberin is an old product, already disclosed in the literature. More precisely, the French BSM 5921M and British Published Specification 1,089,475 have already described the vitaminic properties of this compound and its ability to increase the blood concentration of Vitamin $B_1$. Vitaberin is disclosed as a drug able to counter act the noxious effects of avitaminosis $B_1$. To this purpose Vitaberin is used in the form of tablets containing from 5 to 50 mg of active ingredient per unit dosage.

We have now found that higher dosages of Vitaberin may induce new and surprising pharmacological properties. The pharmaceutical compositions, according to the invention, show psychoanaleptic properties and these properties do not proceed from the previously known Vitaminic properties.

These psychoanaleptic properties have been evidenced both through pharmacological and clinical testing, and therefore the pharmaceutical compositions, according to the present invention, may be used in the treatment of psychic disturbances, alteration of the behaviour, decrease of vigilance, and weakening of the psychic and intellectual tone, in the children as well as in elderly people.

The pharmaceutical compositions according to the invention may also be used in the treatment of the depressive or hypnotic effects due to the administration of tranquillizing drugs, barbiturates, sedative agents, and neuroleptic agents.

They are presented in any of the forms suitable for parenteral, oral, sublingual or rectal administration. Preferably they are presented in the form of tablets, coated tablets, dragees, soft gelatine capsules, capsules, drinkable emulsions, suspensions or solutions, injectible solutions, sublingual tablets and suppositories.

They contain from 150 to 500 mg of active ingredient and preferably from 200 to 400 mg of Vitaberin per unit dosage.

For this purpose the daily dosage will range broadly depending on the age of the patient, the illness to be treated and the route of administration. It may vary from 200 to 1500 mg per day in the man and preferably from 400 to 1200 mg when administered perorally.

The inert carriers required for the production of said pharmaceutical compositions may include for the dry pharmaceutical compositions : starches, modified starches, hydrolysed starches, talc, lactose, glucose, mannitol, silica dioxide, titanium oxide, calcium carbonate, magnesium phosphate, or sugar. They may also incorporate binders, extenders, diluents, fillers, emulsifiers, tensioactive agents such as methyl cellulose, carboxymethyl cellulose, ethylcellulose, polyvinylpyrrolidone, polyoxyethylene sorbitan mono oleates sold under the Trade Names "Spans" or "Tweens", or a glyceryl mono-oleate.

For the preparations in a liquid form, water, saline isotonic solutions, glycerol, or ethanol may be suitable.

For the rectal way, the suppositories are made from cocoa butter, or polyethylene oxide stearates. In general the pharmaceutical compositions according to the invention may also include a natural colouring matter such as $\beta$-carotene, xantrophyll or canthaxanthine, an artificial colouring matter such as orange yellow S lack; a sweetening agent, a flavouring agent.

More suitably the tablets may be coated by spraying or incorporating thereon, for example, solutions of waxes, butyl phthalate or aluminium 2-methyl hexanoate in a readily volatile solvent.

The following examples are merely intended to evidence the psychoanaleptic properties of the pharmaceutical compositions according to the invention, on the basis of pharmacological tests as well on the basis of clinical trials.

EXAMPLE I

| Coated tablets containing 400 mg Vitaberin per unit dosage | |
|---|---|
| Vitaberin | 4050 g |
| Maize starch | 200 g |
| Sodium carboxymethyl cellulose | 100 g |
| White beewax | 100 g |
| Dry maize starch | 50 g |
| Ethyl cellulose | 50 g |
| Glucose | 50 g |
| Lactose | 250 g |
| Laque jaune orange S | 100 mg |
| Magnesium stearate | 200 g |
| Polyoxyethylene sorbate | 40 g |
| Polyvinyl pyrrolidone | 50 g |
| Colloidal silica | 50 g |
| Sugar | 30 g |
| Talc | 40 g |
| Titanium oxide | 40 g |

They are made, according to known methods, 10,000 tablets coated with wax, finished at 0.525 g each.

EXAMPLE II

| Coated tablets containing 250 mg Vitaberin per unit dosage | |
| --- | --- |
| Vitaberin | 2010 g |
| Maize Starch | 1400 g |
| Sodium carboxymethyl cellulose | 100 g |
| White wax | 100 g |
| Dry maize starch | 250 g |
| Ethyl cellulose | 25 g |
| Glucose | 25 g |
| Lactose | 250 g |
| Gelatin | 100 g |
| Magnesium stearate | 200 g |
| Glyceryl mono-oleate | 40 g |
| Polyethylene glycol sorbate | 40 g |
| Polyvinyl pyrrolidone | 40 g |
| Colloidal silica | 50 g |
| Sugar | 100 g |
| Talc | 300 g |
| Titanium oxide | 25 g |

There are obtained about 10,000 tablets finished at 0.5 g. each.

EXAMPLE III

| Suppositories containing 400 mg Vitaberin per unit dosage | |
| --- | --- |
| Vitaberin | 415 g |
| Polyethylene glycol stearate | 400 g |
| Cacoa butter | 1850 g |
| Canthaxanthine | 0 g5 |
| for 1,000 suppositories finished at | 2.75 g. each. |

EXAMPLE IV

Pharmacological study of the pharmaceutical compositions according to the invention

Technique

The experimental test is performed with a labyrinth including a corridor; it is 2.60 m long, and 1 m wide; each corridor is 0.13 m wide. The learning of many rats is performed, after fasting of the animals for 48 hours, by running over the corridor until they reach a box containing food. When the animals reach it, they are allowed to remain there only a very short time in order that they can only nibble a small amount and thereby avoid too rapid a satiatian.

During the testing period, each animal has to run over tha labyrinth five times, once every 10 minutes. The measures for each testing represent the average of five consecutive runs. Further, the number of mistakes i.e. the number of times the animals deviate from the traject and come back to avoid a closed path, and the percentage of negative tests, are determined.

Moreover many controls have been studied in order to determine whether the normal rat is able to improve its performances or not. After having repeated the tests on the day 5 and day 9, it appears a slight increase of time for running over

| Controls: | day 1 | 46.7 s | |
| --- | --- | --- | --- |
| | day 5 | 54.8 s | |
| | day 9 | 65.7 s | (P=0.1) |

In the controls the number of mistakes appear without variation. The percentage of negative tests increases slightly [day 1=17.5 day 9=26.75 (P=0.1)]

Therefore it has been stated that in the controls, a statistically significant decrease in learning occurs during a period of 10 days without strengthening.

Results a) Pharmaceutical compositions of Vitaberin 30 mg/kg a day for 10 days perorally

| | | | |
| --- | --- | --- | --- |
| $D_1$: | time for running over | 73.3 s | |
| | number of mistakes/test | 1.33 | |
| | percentage of negative tests | 22.5 | |
| $D_5$: | time for running over | 32.9 | (P=0.05) |
| | number of mistakes | 0.5 | |
| | percentage of negative tests | 0 | (P=0.05) |
| $D_9$: | time for running over | 37.8 | (P=0.05) |
| | number of mistakes | 0.75 | |
| | percentage of negative tests | 0 | (P=0.05) | b) Pharmaceutical compositions of Vitaberin 30 mg/kg a day for 10 days perorally after having been taught for 10 days and allowed to rest for 15 further days

| | | | |
| --- | --- | --- | --- |
| $D_{10}$: | time for running over | 30.6 s | after learning |
| | number of mistakes | 0.64 | |
| | percentage of negative tests | 2 | |
| $D_{25}$: | time for running over | 86.7 s | after 15 days resting |
| | number of mistakes | 1.37 | |
| | percentage of negative tests | 31.25 | |
| $D_{30}$: | time for running over | 70.5 s | |
| | number of mistakes | 0.78 | |
| | percentage of negative tests | 8.3 | (P=0.02) |
| $D_{34}$: | time for running over | 52.8 s | (P=0.1) |
| | percentage of negative tests | 8.3 | (P=0.05) |

The pharmaceutical compositions of Vitaberin show very significative effects on the learning and the recovery of the memories in the rats.

Clinical Experiments with the Pharmaceutical Compositions of Vitaberin

A. Treatment of the depressive state in the drug-addict after having been deprived of drug The deprivation is performed using tranquillizers or neuroleptic drugs. In most cases the drug-habit seems to objectively disappear after 6 to 20 days of treatment, but the risk of relapse is very high due to psychological syndromes, state of insomnia and anguish.

The pharmaceutical compositions according to the invention have been administered to 70 drug-addicts which have been previously deprived of drug in a hospital. 48 of them are men, 22 are women. The average age is 24.7 years old.

The useful posology ranged from 400 mg (1) to 1200 mg (eight times) in two administrations per day. In some cases the posology was decreased from 1000 / or 800 mg to 600 mg a day; in one case it was increased from 600 to 1000 mg.

The pharmaceutical compositions of Vitaberin show a great efficacy in the psychological depression after deprivation:

41 out of 50 cases in the psychasthenia after deprivation of drug (82%)

28 out of 35 cases in the disturbances of the watchfullness (80%) due to administration of tranquillizers 13 out of 19 cases in the depressive state after deprivation (68.4%)

B. Study of the psychoanaleptic activity in children showing asthenia

These children have been divided into 5 groups:

The mental defectives showing an asthenic syndrome with predominating psychological disturbance (27 cases)

The normal children showing an asthenic syndrome predominantly from psychic origin (13 cases)

The children showing an asthenic syndrome of complex meaning (15 cases)

The children showing an asthenic syndrome physically and psychically-evidenced correlated to an intercurrent illness (10 cases)

The children showing a depressive state (6 cases)

The usual posology ranged from 200 mg (4 cases) to 600 mg (1 case) perorally. The treatment lasted from 1 week to 2 months with an average length of 3–4 weeks.

Among the 71 cases experimented, the clinical trial has given the following results:
  very good results: 26 cases
  good results: 24 cases
  insufficient improvement: 14 cases
  no improvement: 7 cases Biological and clinical tolerance has been found very good.

C. Study of the psychoanaleptic effect in the man for the treatment of psychasthenia For this group of experiments 80 cases have been gathered. 37 of them related to patients suffering from chronic somatic affections, mostly arising from old age; 29 of them related to patients suffering from depressive state and neurotic conditions; 14 of them related to patients suffering from "counter-acting" asthenia (reactional asthenia).

The usual daily posology ranged from 400 to 800 mg by oral way either on constant rate or on variable rate. The treatment lasted an average of 4 weeks.

The therapeutic results have been as follows:
  very good and good results: 51 (64%)
  average improvement: 17
  no improvement: 12

Vitaberin thus appears to be very efficient in the treatment of reactional depressive state caused by emotional disturbances either in improving tolerance of tranquilizing drugs and counter-acting the side-effects thereof or helping the patients in healing and provoking more quickly the full recovery when anti-depressive agents have been simultaneously administered to the patients.

D. Psychoanaleptic effect of Vitaberin in elderly people

The clinical trial has been carried out on 46 elderly people having the average age of 83 years.

They suffered mainly from physical and intellectual senility and the study was drawn to the improvement of the behaviour and the psychical efficiency.

The daily posology has been fixed for every patient at 600 mg in the form of 3 tablets given regularly during the day. The treatment lasted from 4 to 10 weeks.

The elderly people have been studied on a psychometric basis through the test of Wechsler-Bellevue (test of information) before and after treatment.

The studied symptoms have been improved as follows:
  tiredness: 15 out of 18
  mood: 14 out of 19
  behaviour: 8 out of 11
  quality of the sleep: 17 out of 21
  sociability: 12 out of 17
  memory: 31 out of 36
  attentiveness: 27 out of 32
  vigilance: 27 out of 33
  quality of the ideation: 23 out of 28

From a psychometrial point of view the results have been as follows on 46 patients:
  excellent: 13 patients
  good: 11 patients
  useful: 13 patients
  none: 5 patients
  no change: 4 patients Broadly, after administration of 600 mg per day of Vitaberin, the psychometrial study evidences the improvement of the memory, of the attentiveness, of the ideation and of the vigilance in 37 patients out of 46.

What I claim is:

1. A method for treating depressive state in a human subject, and resulting psychic weakness and behavioural disturbance, which consists in administering parenterally, orally, sublingually, or rectally to said subject an amount of bis [(isobutyryloxyethyl) methylene] bis N-[(4-amino 2-methyl 5-pydimidinyl) methyl] formamide disulphide which is effective for said purpose.

2. The method according to claim 1 wherein the amount of active ingredient ranges from 3.3 mg/kg to 25 mg/kg. daily.

* * * * *